United States Patent [19]

Jenck

[11] Patent Number: 4,521,614

[45] Date of Patent: Jun. 4, 1985

[54] CARBONYLATION OF MONOOLEFINS

[75] Inventor: Jean Jenck, Villeurbanne, France

[73] Assignee: Rhone-Poulenc Chimie De Base, Courbevoie, France

[21] Appl. No.: 491,040

[22] Filed: May 3, 1983

[30] Foreign Application Priority Data

May 7, 1982 [FR] France .................. 82 08120

[51] Int. Cl.$^3$ .............................. C07C 67/38
[52] U.S. Cl. .................... 560/193; 560/130;
560/146; 560/180; 560/187; 560/192; 560/198;
560/204; 560/226; 560/228; 560/233
[58] Field of Search ........... 560/130, 146, 180, 187,
560/192, 193, 198, 204, 226, 228, 233; 502/171,
325

[56] References Cited

U.S. PATENT DOCUMENTS

| | | | |
|---|---|---|---|
| 3,507,891 | 4/1970 | Hearne et al. | 560/204 X |
| 3,778,466 | 12/1973 | Matsuda | 560/204 X |
| 3,856,832 | 12/1974 | Ethyl | 560/204 X |
| 4,171,451 | 10/1979 | Kummer et al. | 560/204 |
| 4,212,989 | 7/1980 | Isshiki et al. | 560/232 |

Primary Examiner—Natalie Trousof
Assistant Examiner—Vera C. Clarke
Attorney, Agent, or Firm—Burns, Doane, Swecker & Mathis

[57] ABSTRACT

Esters, e.g., alkyl adipates, are facilely prepared by carbonylation among an alcohol, carbon monoxide and a monoolefin, e.g., an alkyl pentenoate, in the presence of a catalytically effective amount of cobalt and a tertiary nitrogen base, and optionally hydrogen, said reaction being carried out in an aromatic hydrocarbon reaction medium bearing from 1 to 3 nuclear substituents, and said substituents comprising cyano or a radical of the formula R—Y— having up to 20 carbon atoms, wherein Y is a direct valence bond, an oxygen atom, a sulfur atom, a carbonyl group or a carbonyloxy group (—CO—O—), with R being bonded to the oxygen of the group —CO—O—, and R is alkyl, aralkyl or or aryl, or a cyano substituted such R—Y— radical, or a radical R—Y— which includes one of the divalent bridges —O—, —CO— or —CO—O— along its skeletal carbon chain, with the proviso that at least one of said substituents is either cyano or a radical R—Y— wherein Y is other than a direct valence bond.

21 Claims, No Drawings

CARBONYLATION OF MONOOLEFINS

BACKGROUND OF THE INVENTION

1. Field of the Invention

The present invention relates to the preparation of esters by the carbonylation of monoolefinic compounds, namely, by reacting carbon monoxide and an alcohol with compounds containing a single olefinic double bond, and, more especially, relates to the preparation of diesters from alkyl pentenoates, e.g., the synthesis of alkyl adipates by the carbonylation of alkyl pentenoates.

2. Description of the Prior Art

It is well known to this art from *Bulletin of the Chemical Society of Japan*, Volume 46, pages 526 and 527 (1973), that a mixture containing alkyl diesters, and in particular an alkyl adipate, is obtained by reacting carbon monoxide and an alcohol with an alkyl pen-3-enoate under high pressure and at elevated temperature, in the presence of cobalt carbonyl and a heterocyclic aromatic nitrogen base. However, the industrial-scale development of such a technique, the value of which is not contested in principle, is greatly jeopardized not only by the poor efficiency of the catalyst system, but also by the considerable proportion of alkyl pentanoate formed, even though the reaction is carried out in the absence of hydrogen.

Furthermore, it too is well known to this art that the presence of small amounts of hydrogen in the reaction medium tends to increase the efficiency of cobalt-based catalysts in processes for the synthesis of esters by reacting an alcohol and carbon monoxide with an olefinic compound.

It has nevertheless been found that, in the majority of cases, this favorable effect associated with the presence of small amounts of hydrogen is accompanied by an adverse influence on the selectivity in respect of linear esters, which are the specifically intended products.

In fact, it has been observed that the presence of hydrogen not only tends to increase the proportion of hydrogenation products in the reaction mixture, but also is capable of reducing the proportion of linear ester in the esters formed.

This adverse effect greatly compromises the economics of these processes, insofar as the utilization of the branched esters and the hydrogenation product is uncertain or even nonexistent. This is the case, in particular, of the branched diesters and the alkyl pentanoates produced during the carbonylation of alkyl pentenoates. In fact, as these products are destroyed in practice, their formation in effect corresponds to an intolerable loss of starting material. Furthermore, hydrogen can be formed in situ from the traces of water which may be contained in technical-grade reactants, according to the well-known reaction:

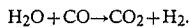

$H_2O + CO \rightarrow CO_2 + H_2$.

For obvious economic reasons, it would be desirable to be able to use technical-grade carbon monoxide containing hydrogen, without this being to the detriment of the selectivity in respect of linear esters, which are the desired final products. It would also be desirable, for the same reasons, to be able to use reactants containing traces of water, without this contributing to a loss in starting material.

SUMMARY OF THE INVENTION

Accordingly, a major object of the present invention is the provision of an improved process for the selective preparation of linear esters by reacting an alcohol and carbon monoxide with a compound containing a single olefinic double bond, in the presence of cobalt and a tertiary nitrogen base, which improved process is conspicuously devoid of those disadvantages and drawbacks to date characterizing the state of this art, and which features carrying out the reaction in an aromatic hydrocarbon which contains from 1 to 3 substituents selected from among the cyano group and the radicals of the formula R—Y—, in which Y represence a valence bond, an oxygen atom, a sulfur atom, a carbonyl group or a carbonyloxy group (—CO—O—), the radical R being attached to the oxygen atom of (—CO—O—), and wherein R represents an alkyl, aralkyl or aryl radical; the said radical R, which can optionally contain a cyano substituent or a divalent bridge —O—, —CO— or —CO—O— inserted along the basic carbon chain or backbone, contains at most 20 carbon atoms; at least one of the substituents is selected from among the cyano group and the radicals R—Y in which Y is not a valence bond.

DETAILED DESCRIPTION OF THE INVENTION

More particularly according to the present invention, carbon monoxide and an alcohol R′—OH are reacted with a compound of the formula $R_1CH=CHR_2$, in which:

(i) $R_1$ and $R_2$, which are identical or different, are each hydrogen or an alkyl radical having at most 20 carbon atoms, which can be substituted by 1 or 2 chlorine atoms or alkoxy groups containing at most 4 carbon atoms;

(ii) it also being possible for $R_1$ to represent a radical $—(CH_2)_p—COOH$, $—(CH_2)_p—COOR_3$ or $—(CH_2)_p—CN$, in which p is an integer equal to at most 6 and capable of being zero, and $R_3$ represents an alkyl radical containing at most 12 carbon atoms, it also being possible for one to two methylene groups to contain an alkyl substituent having at most 4 carbon atoms; and (iii) it also being possible for $R_1$ and $R_2$ to together form a single divalent radical $—(CH_2)_q—$, if appropriate containing one or two alkyl substituents having at most 4 carbon atoms, q being an integer ranging from 3 to 6 inclusive; and (iv) R′ is an alkyl radical containing at most 12 carbon atoms, which is optionally substituted by one or two hydroxyl groups, a cycloalkyl radical having from 5 to 7 carbon atoms, an aralkyl radical having from 7 to 12 carbon atoms or a phenyl radical.

Thus, the starting materials which can be carbonylated according to the present process are compounds containing a single internal or terminal olefinic double bond; these compounds more specifically contain from 3 to 20 carbon atoms.

Carrying out the subject process makes it possible to obtain saturated esters, namely, compounds which contain on the one hand a carboxylate group (—COOR′) and on the other hand one hydrogen atom more than the starting material. Among these esters, the compound in which the carboxylate group (—COOR′) is situated at the terminal position on the main chain of the starting material is predominant.

A first category of starting materials which is more particularly suitable has the formula: $R_1CH=CHR_2$ in which $R_1$ and $R_2$, which are identical or different, are each hydrogen or an alkyl radical having at most 10 carbon atoms, or together form a single divalent radical $-(CH_2)_q-$, q being as defined above, it being possible, if appropriate, for the said radical to contain 1 or 2 methyl substituents. Examples of such compounds which are representative are propylene, but-1-ene, but-2-ene, hexenes, octenes, and dodec-1-ene.

A second category of starting materials which is more particularly suitable comprises the compounds of the formula: $R_1CH=CHR_2$ in which $R_1$ represents a radical $-(CH_2)_p-COOR_3$, p and $R_3$ also being as defined above, it also being possible for one to two methylene groups to contain an alkyl substituent having at most 4 carbon atoms, and $R_2$ represents hydrogen or an alkyl radical having at most 4 carbon atoms.

Among the compounds of this type, the alkyl pentenoates are very particularly valuable because they make it possible to obtain alkyl adipates, which are intermediates for adipic acid.

The present process requires the use of an alcohol of the formula R'OH, with R' also being as above defined.

Examples of alcohols which are advantageously employed in the subject process are methanol, ethanol, isopropanol, n-propanol, tert.-butanol, n-hexanol, cyclohexanol, 2-ethylhexan-1-ol, dodecan-1-ol, ethylene glycol, hexane-2,6-diol, benzyl alcohol, phenylethyl alcohol and phenol.

It is preferred to use an alkanol having at most 4 carbon atoms; methanol and ethanol are especially suitable for carrying out the subject process.

The alcohol and the monoolefinic compound can be used in stoichiometric amounts. However, it is preferred to use an excess of alcohol in the proportion of 1 to 10 or, more preferably, 2 to 5 mols of alcohol per mol of monoolefinic compound.

The reaction is carried out in the presence of cobalt. Any source of cobalt which is capable of reacting with carbon monoxide in the reaction medium to provide cobalt carbonyl complexes in situ can be used within the scope of the invention.

Examples of typical sources of cobalt are finely divided cobalt metal, inorganic salts, such as cobalt nitrate or carbonate, and organic salts, in particular carboxylates. Cobalt carbonyl or hydrocarbonyls can also be used; dicobalt octacarbonyl is suitable for carrying out the present process.

The molar ratio of the monoolefinic compound to the cobalt typically ranges from 10 to 1,000. This ratio is advantageously set at a value ranging from 20 to 300.

The process according to the present invention also requires the presence of a tertiary nitrogen base, most preferably having a $pK_a$ ranging from 3 to 10.

Preferred are the 5-membered to 6-membered nitrogen heterocyclic compounds which can contain one or two substituents selected from among alkyl or alkoxy groups having at most 4 carbon atoms, the hydroxyl group and halogen atoms, which optionally contains 2 or 3 double bonds and which, if appropriate, can furthermore be fused to a benzene nucleus, with the proviso that the ring members adjacent to the nitrogen heteroatom are neither substituted nor common to two rings.

6-membered nitrogen heterocyclic compounds having a $pK_a$ ranging from 4 to 7, in particular pyridine, 4-picoline, isoquinoline and 3,5-lutidine, are more particularly preferred for carrying out the subject process.

The amount of tertiary nitrogen base used is generally such that the molar ratio N/Co ranges from 1 to 50. To carry out the invention with notably good results, it is preferred that this ratio be set at a value ranging from 2 to 25.

One of the essential characteristics of the process according to the invention is the use, as reaction solvent, of an aromatic hydrocarbon which contains from 1 to 3 substituents selected from among the cyano group and the radicals of the formula $R-Y-$, in which Y represents a valence bond, an oxygen atom, a sulfur atom, a carbonyl group or a carbonyloxy group ($-CO-O-$), the radical R being attached to the oxygen atom of ($-CO-O-$), and R represents an alkyl, aralkyl or aryl radical; the said radical R, which can optionally contain a cyano substituent or a divalent bridging moiety $-O-$, $-CO-$ or $-CO-O-$ inserted in the basic carbon chain, contains at most 20 carbon atoms; at least one of the substituents is selected from among the cyano group and the radicals $R-Y$ in which Y is not a valence bond.

More specifically, representative solvents have the general formula:

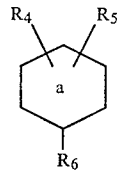

in which a is a benzene or naphthalene nucleus, $R_4$ represents a cyano group or a radical $R-Y-$, with R and Y being as defined above and Y not being a valence bond, and $R_5$ and $R_6$, which are identical or different, are each a hydrogen atom, a cyano group or a radical $R-Y-$, with R and Y also being as defined above and it being possible for Y to represent a valence bond. Preferably, one of the radicals $R_5$ and $R_6$ represents hydrogen or a radical $R-Y-$ in which Y is a valence bond and R is an alkyl radical having at most 4 carbon atoms.

If Y represents an oxygen atom, a sulfur atom or a carbonyl group, R is more preferably selected from among alkyl, aralkyl or aryl radicals containing at most 10 carbon atoms, and R is preferably an alkyl radical which contains at most 4 carbon atoms.

If Y represents an carbonyloxy group ($-CO-O-$), R is identical to the radical R' of the alcohol used as the starting material.

If Y represents a valence bond, R is more preferably selected from among alkyl or aralkyl radicals which have at most 10 carbon atoms and which can contain a divalent bridging moiety $-O-$, $-CO-$ or $-CO-O-$ inserted along the basic carbon chain, with the proviso that R is selected to be identical to R' if a carbonyloxy bridge is inserted in the chain; R can also be a phenyl radical optionally substituted by 1 to 3 alkyl radicals having at most 4 carbon atoms.

Preferably, a is a benzene nucleus. $R_4$ is advantageously a radical $R-Y-$ in which Y represents an oxygen or sulfur stom and R is an alkyl radical which contains at most 4 carbon atoms or a phenyl radical. $R_5$ and $R_6$ preferably each represent a hydrogen atom.

Of course, it is possible to use mixtures of a plurality of these aromatic compounds.

Exemplary of solvents which are suitable for carrying out the process according to the invention are: methoxybenzene (anisole), benzonitrile, methylthiobenzene (thioanisole), ethoxybenzene (phenetole), diphenyl ether, diphenyl sulfide, phenyl benzyl ether, phenyl benzyl sulfide, acetophenone, propiophenone, n-butyl phenyl ketone, methyl benzoate, n-butyl benzoate, phenyl benzoate, p-toluonitrile, 2-methoxytoluene, 2-ethoxytoluene, p-methylacetophenone, methyl p-toluate, 1,2-dimethoxybenzene (veratrole), 1,3-diethoxybenzene, 1,4-dimethoxybenzene, dimethyl terephthalate, methyl p-methoxybenzoate, methyl p-ethylthiobenzoate, 3,5-dimethylacetophenone and its isomers, 1,3,5-trimethoxybenzene and the like.

Anisole and thioanisole are particularly preferred for carrying out the subject process.

The amount of solvent, which influences the selectivity of the reaction, will generally constitute more than 20% (by weight) of the initial reaction mixture, and, to carry out the subject process with good results, it will range from 30 to 60% (by weight) of the said mixture.

In a preferred embodiment of the process of the invention, the reaction is also carried out in the presence of hydrogen. Within the scope of this embodiment, the hydrogen will represent at least 0.1% (by volume) of the carbon monoxide, but without exceeding 3% (by volume). Preferably, the hydrogen content will represent from 0.5 to 2% (by volume) of the carbon monoxide.

Of course, although the hydrogen can be conveniently introduced into the reaction medium in the form of a mixture with the carbon monoxide, it can also be supplied separately.

The reaction is carried out in the liquid phase at a temperature above 120° C., there being no advantage in exceeding 200° C., under a carbon monoxide pressure of at least 50 bars and capable of reaching 1,000 bars. The reaction is preferably carried out at a temperature on the order of 130° to 180° C. and under a carbon monoxide pressure on the order of 100 to 300 bars.

Of course, the optimum pressure and temperature conditions will be the more severe, the less reactive the starting material, this being the case, in particular, as the degree of steric protection of the double bond increases.

In addition to the hydrogen, the carbon monoxide used can also contain impurities such as carbon dioxide, methane and nitrogen.

As above indicated, the process according to the present invention has a more particularly advantageous application in the synthesis of diesters from alkyl pentenoates. In general, an alkyl pent-3-enoate is used, although it is possible to use alkyl pent-2-enoates, alkyl pent-4-enoates and mixtures of alkyl pentenoates.

Within the scope of this invention, it is preferable to select the alcohol (co-reactant) which corresponds to the alkyl radical of the starting ester, the alkyl radical advantageously having at most 4 carbon atoms. Good results are obtained starting from one or the other of the following pairs of reagents: methyl pentenoate and methanol, or ethyl pentenoate and ethanol.

Upon completion of the reaction, or when the desired degree of conversion has been attained, the desired linear ester is recovered by any suitable means, for example, by distillation or liquid/liquid extraction.

In order to further illustrate the present invention and the advantages thereof, the following specific examples are given, it being understood that same are intended only as illustrative and in nowise limitative.

Preparation of Alkyl Adipates

EXAMPLES 1 to 27

Control experiments (a) to (i)

The following conventions are employed below.

The products formed do not include the compounds resulting from the position isomerism of the olefinic double bond.

The products formed are essentially the diesters and the alkyl pentanoate, the latter resulting from the hydrogenation of the starting material ester.

A denotes the activity, expressed in mols of products formed per hour and per gram atom of cobalt;

X (%) denotes the numbers of mols of diesters per 100 mols of products formed;

Y (%) denotes the number of mols of alkyl adipate per 100 mols of products formed; and Z (%) denotes the number of mols of alkyl pentanoate per 100 mols of products formed.

EXAMPLES 1 to 19

Control experiments (a) to (i)

A series of experiments was carried out according to the following procedure:

Methyl pent-3-enoate (P3), methanol, dicobalt octacarbonyl (DCOC), isoquinoline and, if appropriate, a solvent, were introduced into a 125 ml stainless steel autoclave purged under argon.

The autoclave was then purged with a stream of carbon monoxide, if appropriate containing hydrogen. The autoclave was then heated to the temperature (T) under a pressure (P). After a reaction time (designated by t and expressed in hours) at this temperature, the autoclave was cooled and degassed. The reaction mixture was analyzed by gas chromatography. The particular conditions and also the results obtained are respectively reported in Tables I(A) and I(B) below:

TABLE I(A)

| Ref | P3 mmol | MeOH mmol | DCOC mmol | MeOH/P3 | P3/Co | N/Co | $H_2$ (% by volume) | P bars | T °C. |
|---|---|---|---|---|---|---|---|---|---|
| a | 50.1 | 109 | 1.02 | 2.17 | 24.6 | 4 | 0 | 130 | 160 |
| b | 49.7 | 99 | 0.88 | 1.99 | 28.5 | 4.5 | 0.7 | " | " |
| c | 99.8 | 198 | 2.00 | 1.98 | 25.0 | 12 | 0.9 | " | " |
| d | " | 200 | 2.01 | 2.00 | 24.8 | " | 2.6 | " | " |
| e | 50.3 | 104 | 1.00 | 2.07 | 25.2 | 3.9 | 0.8 | " | " |
| 1 | 50.8 | 102 | 1.00 | 2.01 | 25.4 | 4.0 | 0.8 | " | " |
| 2 | 50.2 | 102 | 1.01 | 2.03 | 24.8 | 4.0 | " | " | " |
| 3 | 50.1 | 101 | 0.96 | 2.01 | 26.0 | 4.3 | " | " | " |
| 4 | 49.3 | 99.4 | 1.04 | 2.02 | 23.6 | 4.0 | " | " | " |
| f | 101 | 196 | 1.97 | 1.94 | 25.6 | 8.1 | " | " | " |
| 5 | 49.8 | 100 | 0.92 | 2.00 | 27.0 | 8.6 | " | " | " |

TABLE I(A)-continued

| Ref | P3 mmol | MeOH mmol | DCOC mmol | MeOH/P3 | P3/Co | N/Co | H$_2$ (% by volume) | P bars | T °C. |
|---|---|---|---|---|---|---|---|---|---|
| g | 49.7 | 98.4 | 1.01 | 1.98 | 24.5 | 7.9 | " | " | 180 |
| 6 | 50.3 | 103 | 0.88 | 2.05 | 28.6 | 9.1 | " | " | " |
| 7 | 50.0 | 98.0 | 0.92 | 1.96 | 27.0 | 8.5 | " | " | " |
| 8 | 50.4 | 101 | 1.04 | 2.01 | 24.0 | 7.8 | " | " | " |
| 9 | 50.5 | 99 | 1.00 | 1.96 | 25.3 | 8.0 | " | " | " |
| 10 | 49.8 | 100 | 1.01 | 2.01 | 24.7 | 4.1 | " | " | " |
| h | 50.1 | 98.8 | 1.00 | 1.97 | 25.1 | 4.0 | " | " | " |
| 11 | 50.3 | 102 | 1.03 | 2.03 | 25.2 | " | " | " | 140 |
| i | 49.7 | 100 | 1.03 | 2.01 | 24.1 | 3.8 | " | " | " |
| 12 | 100 | 202 | 2.07 | 2.02 | 24.2 | 4.0 | " | " | 160 |
| 13 | 50.1 | 100 | 1.02 | 2.00 | 24.6 | 4.0 | " | " | " |
| 14 | 50.0 | 100 | 0.94 | 2.00 | 26.5 | 4.1 | 0.9 | " | 137 |
| 15 | 50.4 | 100 | 1.01 | 1.98 | 24.9 | 3.8 | " | " | 152 |
| 16 | 50.4 | 101 | 1.02 | 2.00 | 24.7 | 8.0 | " | " | 180 |
| 17 | 100 | 1.99 | 1.00 | 1.99 | 50.2 | " | 0.8 | 250 | " |
| 18 | 50.4 | 103 | 0.99 | 2.04 | 25.4 | 3.9 | 2.0 | 130 | 160 |
| 19 | 50.5 | 101 | 0.99 | 2.00 | 25.4 | 12.1 | 0.9 | " | " |

TABLE I(B)

| | SOLVENT | | | | | | |
|---|---|---|---|---|---|---|---|
| Ref. | nature | (% by weight) | t | A | X (%) | Y(%) | Z (%) |
| a | — | 0 | 1 | 3.7 | 95.1 | 79.4 | 4.9 |
| b | — | 0 | " | 10.4 | 89.0 | 74.6 | 10.4 |
| c | — | 0 | " | 1.9 | 94.7 | 75.5 | 4.9 |
| d | — | 0 | " | 3.3 | 92.5 | 74.7 | 6.8 |
| e | — | 0 | 2 | 7.9 | 92.3 | 76.4 | 7.0 |
| 1 | anisole | 49 | 1.5 | 4.7 | 95.0 | 81.1 | 4.6 |
| 2 | DMMB | 50 | 2 | 2.5 | 95.5 | 79.7 | 2.9 |
| 3 | veratrole | 51 | " | 5.1 | 94.4 | 79.4 | 5.1 |
| 4 | benzonitrile | 50 | 4 | 1.7 | 95.2 | 80.5 | 4.5 |
| f | — | 0 | 2 | 2.4 | 94.9 | 76.6 | 4.6 |
| 5 | anisole | 47 | " | 4.6 | 95.6 | 79.6 | 4.0 |
| g | — | 0 | " | 5.6 | 88.0 | 74.8 | 11.6 |
| 6 | anisole | 47 | " | 7.0 | 88.2 | 76.7 | 11.6 |
| 7 | acetophenone | 47 | " | 5.8 | 92.4 | 79.1 | 7.3 |
| 8 | benzonitrile | 46 | " | 1.0 | 91.7 | 81.2 | 8.3 |
| 9 | p-toluonitrile | 45 | " | 2.8 | 92.7 | 80.3 | 7.3 |
| 10 | anisole | 49 | " | 7.8 | 88.6 | 75.0 | 10.0 |
| h | — | 0 | " | 9.3 | 84.6 | 70.9 | 15.2 |
| 11 | anisole | 49 | " | 1.5 | 95.8 | 73.1 | 3.7 |
| i | — | 0 | " | 3.4 | 94.0 | 70.3 | 5.6 |
| 12 | MB | 35 | " | 3.7 | 95.3 | 79.4 | 4.1 |
| 13 | thioanisole | 49 | 1.5 | 2.9 | 96.5 | 83.9 | 3.2 |
| 14 | " | 33 | 2 | 0.9 | 96.2 | 76.1 | 2.8 |
| 15 | " | 50 | " | 2.9 | 96.4 | 83.2 | 3.0 |
| 16 | " | " | " | 5.0 | 92.4 | 79.6 | 7.6 |
| 17 | " | 34 | " | 5.6 | 96.6 | 82.4 | 3.2 |
| 18 | " | 50 | " | 4.4 | 93.7 | 81.1 | 5.2 |
| 19 | " | 45 | " | 1.9 | 96.0 | 80.8 | 3.6 |

In Table I(A), the ratios MeOH/P3, P3/Co and N/Co denote, respectively, the molar ratio of the number of mols of pent-3-enoate to the number of gram atoms of cobalt, and the ratio of the number of mols of isoquinoline to the number of gram atoms of cobalt.

In Table I(B), DMMB denotes 3,5-dimethylmethoxybenzene and MB denotes methyl benzoate.

Control experiments (a) to (d) clearly show that, in the absence of solvent, the presence of hydrogen results in an increase in the efficiency of the cobalt-based catalyst and in a considerable drop in the selectivity in respect of dimethyl adipate.

Examples 1 to 19 show that the simultaneous presence of a solvent according to the invention and of hydrogen makes it possible to obtain dimethyl adipate selectively and efficiently.

EXAMPLES 20 to 27

Using the autoclave and the procedure described above, a series of experiments was carried out on a charge containing 50 millimols of methyl pent-3-enoate (Examples 20 to 22 and 24 to 26) or of methyl pent-2-enoate (P2, Examples 23 and 27), 100 millimols of methanol, 1 millimol of dicobalt octacarbonyl, 8 millimols of isoquinoline and a solvent.

(P3 or P2/Co=25; MeOH/P3 or P 2=2; N/Co=4).

The particular conditions and also the results obtained at 160° C. under 130 bars are reported in Table II below.

TABLE II

| | H$_2$ | | SOLVENT | | | | |
|---|---|---|---|---|---|---|---|
| Ref. | (% by volume) | t | nature | (% by weight) | A | X (%) | Y(%) | Z (%) |
| 20 | 0.8 | 2 | anisole | 9 | 6.5 | 92.9 | 78.6 | 6.6 |
| 21 | " | " | " | 22 | 5.0 | 94.2 | 79.3 | 5.4 |
| 1 | " | 1.5 | " | 49 | 4.7 | 95.0 | 81.1 | 4.6 |
| 22 | " | 4 | " | 49 | 3.4 | 96.2 | 81.8 | 3.8 |
| 23 | 0.7 | 2 | " | 49 | 8.4 | 95.1 | 79.3 | 4.4 |
| 24 | 0.9 | " | thioanisole | 32 | 5.2 | 96.0 | 82.3 | 3.6 |
| 25 | " | " | thioanisole | 50 | 3.1 | 96.5 | 83.5 | 3.0 |
| 26 | " | 4 | thioanisole | 66 | 1.1 | 97.4 | 84.4 | 2.5 |
| 27 | " | 2 | thioanisole | 50 | 6.2 | 95.9 | 82.8 | 3.9 |

Preparation of Dimethyl Pimelate

EXAMPLE 28

Using the autoclave described above and a procedure similar to that described above, an experiment was carried out on a charge consisting of:
(i) 44 millimols of methyl hex-2-enoate;
(ii) 100 millimols of methanol;
(iii) 1.02 millimols of dicobalt octacarbonyl;
(iv) 7.98 millimols of isoquinoline; and
(v) 10.4 g of thioanisole (50% by weight).

After a reaction time of two hours at 160° C., the total pressure at the reaction temperature being maintained constant and equal to 130 bars by periodically introducing additional amounts of carbon monoxide containing 0.8% (by volume) of hydrogen, the following results were obtained:

The degree of conversion (DT) of the methyl hex-2-enoate to carbonylation and hydrogenation products (excluding the products resulting from isomerism of the double bond) was: 34.3%.

The selectivity (Y) of the various products obtained was, respectively:
(1) dimethyl pimelate: 74%
(2) other C₇ diesters: 18.5%
(3) methyl hexanoate: 7.5%

Preparation of Methyl Nonanoate

EXAMPLE 29

Control experiment (j)

Using the autoclave described above and a procedure similar to that described above, two experiments were carried out on a charge comprising:
(i) 50 millimols of oct-2-ene;
(ii) 100 millimols of methanol;
(iii) 1 millimol of dicobalt octacarbonyl; and
(iv) 8 millimols of isoquinoline.

The charge of Example 29 also comprised 10.4 g of thioanisole (50% by weight).

The results obtained in Example 29 and in control experiment (j), respectively, after a reaction time of two hours at 160° C. under a total pressure at the reaction temperature of 130 bars, which was maintained constant by periodically introducing additional amounts of carbon monoxide containing 0.8% (by volume) of hydrogen, are reported in Table III below, in which Y and DC have meanings similar to those given in Example 28.

TABLE III

| Reference | 29 | j |
|---|---|---|
| DC (%) | 29.3 | 63 |
| Y (%) of methyl nonanoate | 84.4 | 81.7 |
| Y (%) of other C₉ esters | 15.1 | 18.0 |
| Y (%) of octane | ≦0.5 | ≦0.3 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a linear ester, which comprises reacting an alcohol and carbon monoxide with a monoolefin in the presence of a catalytically effective amount of cobalt and a tertiary nitrogen base, said reaction being carried out in an aromatic hydrocarbon reaction medium bearing from 1 to 3 nuclear substituents, and said substituents comprising cyano or a radical of the formula R—Y— having up to 20 carbon atoms, wherein Y is a direct valence bond, an oxygen atom, a sulfur atom, a carbonyl group or a carbonyloxy group (—CO—O—), with R being bonded to the oxygen of the group —CO—O—, and R is alkyl, aralkyl or aryl, or a cyano substituted such R—Y— radical, or a radical R—Y— which includes one of the divalent bridges —O—, —CO— or —CO—O— along its skeletal carbon chain, with the proviso that at least one of said substituents is either cyano or a radical R—Y— wherein Y is other than a direct valence bond.

2. The process as defined by claim 1, said reaction also being carried out in the presence of hydrogen.

3. The process as defined by claim 1, said aromatic hydrocarbon reaction medium having the general formula:

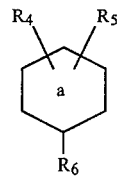

wherein a is benzene or naphthalene, R₄ is cyano or a radical R—Y—, with Y being other than a direct valence bond, and R₅ and R₆, which are either identical or different, are each hydrocarbon, cyano or a radical R—Y—.

4. The process as defined by claim 2, said aromatic hydrocarbon reaction medium having the general formula:

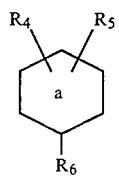

wherein a is benzene or naphthalene, R₄ is cyano or a radical R—Y—, with Y being other than a direct valence bond, and R₅ and R₆, which are either identical or different, are each hydrogen, cyano or a radical R—Y—.

5. The process as defined by claim 3, wherein either R₅ or R₆ is hydrogen or a radical R—Y— in which R is alkyl having up to 4 carbon atoms.

6. The process as defined by claim 3, wherein a is benzene.

7. The process as defined by claim 5, wherein R₄ is a radical R—Y— in which Y is oxygen or sulfur and R is alkyl having up to 4 carbon atoms.

8. The process as defined by claim 5, wherein R₅ and R₆ are each hydrogen.

9. The process as defined by claim 1, wherein said aromatic hydrocarbon comprises at least 20% by weight of the beginning reaction mixture.

10. The process as defined by claim 9, wherein said aromatic hydrocarbon comprises from 30 to 60% by weight of the beginning reaction mixture.

11. The process as defined by claim 2, the hydrogen comprising up to 3% by volume of the carbon monoxide.

12. The process as defined by claim 1, the atomic ratio N/Co ranging from 1 to 50.

13. The process as defined by claim 12, said atomic ratio ranging from 2 to 25.

14. The process as defined by claim 12, the reaction temperature ranging from 120° to 200° C.

15. The process as defined by claim 14, the reaction pressure ranging from 50 to 1,000 bars.

16. The process as defined by claim 1, said tertiary nitrogen base having a pK$_a$ ranging from 3 to 10.

17. The process as defined by claim 1, said monoolefin having the general formula R₁CH=CHR₂, in which R₁ is hydrogen, alkyl having up to 20 carbon atoms or a substituted such alkyl radical bearing 1 or 2 chlorine or alkoxy substituents, with each alkoxy substituent having up to 4 carbon atoms, —(CH₂)$_p$—COOH, —(CH₂)$_p$—COOR₃ or —(CH₂)$_p$—CN, wherein p is an integer ranging from 0 to 6, R₃ is alkyl having up to 12 carbon atoms, and further wherein 1 or 2 of said methylene groups —(CH$_2$)— may bear an alkyl substituent having up to 4 carbon atoms, and R$_2$, which may be identical to or different from R$_1$, is hydrogen, alkyl having up to 20 carbon atoms or a substituted such alkyl radical bearing 1 or 2 chlorine or alkoxy substituents, with each alkoxy substituent having up to 4 carbon atoms, with the proviso that R$_1$ and R$_2$ may together form a single divalent radical —(CH$_2$)$_q$—, in which q is an integer ranging from 3 to 6, or a substituted such divalent radical bearing 1 or 2 alkyl substituents having up to 4 carbon atoms.

18. The process as defined by claim 17, said alcohol having the general formula R'OH, in which R' is alkyl having up to 12 carbon atoms or a substituted such alkyl radical bearing 1 or 2 hydroxyl substituents, cycloalkyl having from 5 to 7 carbon atoms, aralkyl having from 7 to 12 carbon atoms, or phenyl.

19. The process as defined by claim 18, the molar ratio of the monoolefin to cobalt ranging from 10 to 1,000.

20. The process as defined by claim 18, said aromatic hydrocarbon reaction medium comprising methoxybenzene, benzonitrile, methylthiobenzene, ethoxybenzene, diphenyl ether, diphenyl sulfide, phenyl benzyl ether, phenyl benzyl sulfide, acetophenone, propiophenone, n-butyl phenyl ketone, methyl benzoate, n-butyl benzoate, phenyl benzoate, p-toluonitrile, methoxytoluene, ethoxytoluene, methylacetophenone, methyl toluate, dimethoxybenzene, diethoxybenzene, dimethoxybenzene, dimethyl terephthalate, methyl methoxybenzoate, methyl ethylthiobenzoate, dimethylacetophenone or trimethoxybenzene.

21. The process as defined by claim 18, said monoolefin comprising an alkyl pentenoate.

* * * * *